United States Patent [19]

Kaneko

[11] 4,208,581
[45] Jun. 17, 1980

[54] RADIOACTIVE RAY GAUGE

[75] Inventor: Masao Kaneko, Tokyo, Japan

[73] Assignee: Kabushiki Kaisha Daini Seikosha, Tokyo, Japan

[21] Appl. No.: 849,900

[22] Filed: Nov. 9, 1977

[30] Foreign Application Priority Data

Nov. 9, 1976 [JP] Japan .................................. 51/134474

[51] Int. Cl.² ........................ G01T 1/16; H01J 39/00
[52] U.S. Cl. .................................. 250/277 R; 250/308
[58] Field of Search .............................. 250/277, 308

[56] References Cited

U.S. PATENT DOCUMENTS 3,499,152   3/1970   Hetenhouser .................... 250/277 R Primary Examiner—Alfred E. Smith
Assistant Examiner—T. N. Grigsby
Attorney, Agent, or Firm—Robert E. Burns; Emmanuel J. Lobato; Bruce L. Adams

[57] ABSTRACT

In a radioactive ray gauge system, a measuring head continuously detects the thickness of coated material on an advancing sheet. The head has a non-contact type sheet surface-to-head distance detector thereon. The distance detector continuously detects the distance so as to maintain the distance constant thereby eliminating error in the thickness measurement caused by sheet thickness variation, sheet-bending, warping or fluttering.

2 Claims, 2 Drawing Figures

FIG. 2 is a schematic view showing the technique of measuring the thickness of the advancing sheet according to this invention.

RADIOACTIVE RAY GAUGE

BACKGROUND OF THE INVENTION

This invention relates to a radioactive ray gauge suitable for measuring the thickness of metal coatings or the thickness of paint on ON-Line systems.

The radioactive ray gauges have come into use in recent years for measuring continuously the thickness of metal coatings. This measuring process comprises steps of providing a primary radioactive ray (excited X-ray) to the surface of steel sheet after coating, measuring the intensity of a secondary radioactive ray (fluorescent X-ray) and detecting continuously the metal coating with the measured intensity.

However, it is disadvantageous that the conventional measuring head (which carries the radioactive ray detector) produces fluctuating errors of the measured value due to any one or some combination of the phenomenon: thickness variation of the advancing sheet to be measured; bending or warping of the sheet; and which pass line flutter produces the variation of the dynamic distance between the sheet and the measuring head since the conventional measuring head is fixed apart from the advancing sheet.

Accordingly, conventionally, by improving the collimeter or the like disposed in the measuring head, the error in the measurement caused by the variation of the distance between the sheet and the measuring head can be reduced to a more acceptable range.

However, in this system, it is difficult from the technical point to obtain enough compensated characteristic in case the variation of the distance between the sheet and the measuring head is too large.

Besides, the intensity of the secondary radioactive ray which is detected by the measuring head decreases when the above improvement is made.

In the radioactive ray gauge in the ON-Line system, it is necessary that the intensity of the secondary radioactive ray to be obtained as the input signal is as great as possible so that the measuring time is reduced and the intensity of the secondary ray exists in the required statistical variation error range.

At this point, too, it is difficult that the above problems are dissolved since the intensity of the secondary radioactive ray measured in the aforementioned improvement of the characteristic also becomes lower.

Needless to say, the intensity of the secondary radioactiver ray is increased if the intensity of the primary radioactive ray increases.

However, this increase is not desired from the safety point of view. Therefore, it is an object of the invention to provide a radioactive ray gauge for making precise measurement, and eliminating the effect depending on the dynamic variation of the distance between the sheet surface and the measuring head caused by sheet thickness variation, sheet bending, fluttering or the like, on the ON-Line system, provided with the correcting mechanism which corrects the relative position of the measuring head to the sheet surface in response to-and-fro movement of the sheet surface against the head.

DETAILED DESCRIPTION OF PREFERRED EMBODIMENT

Figure 1:
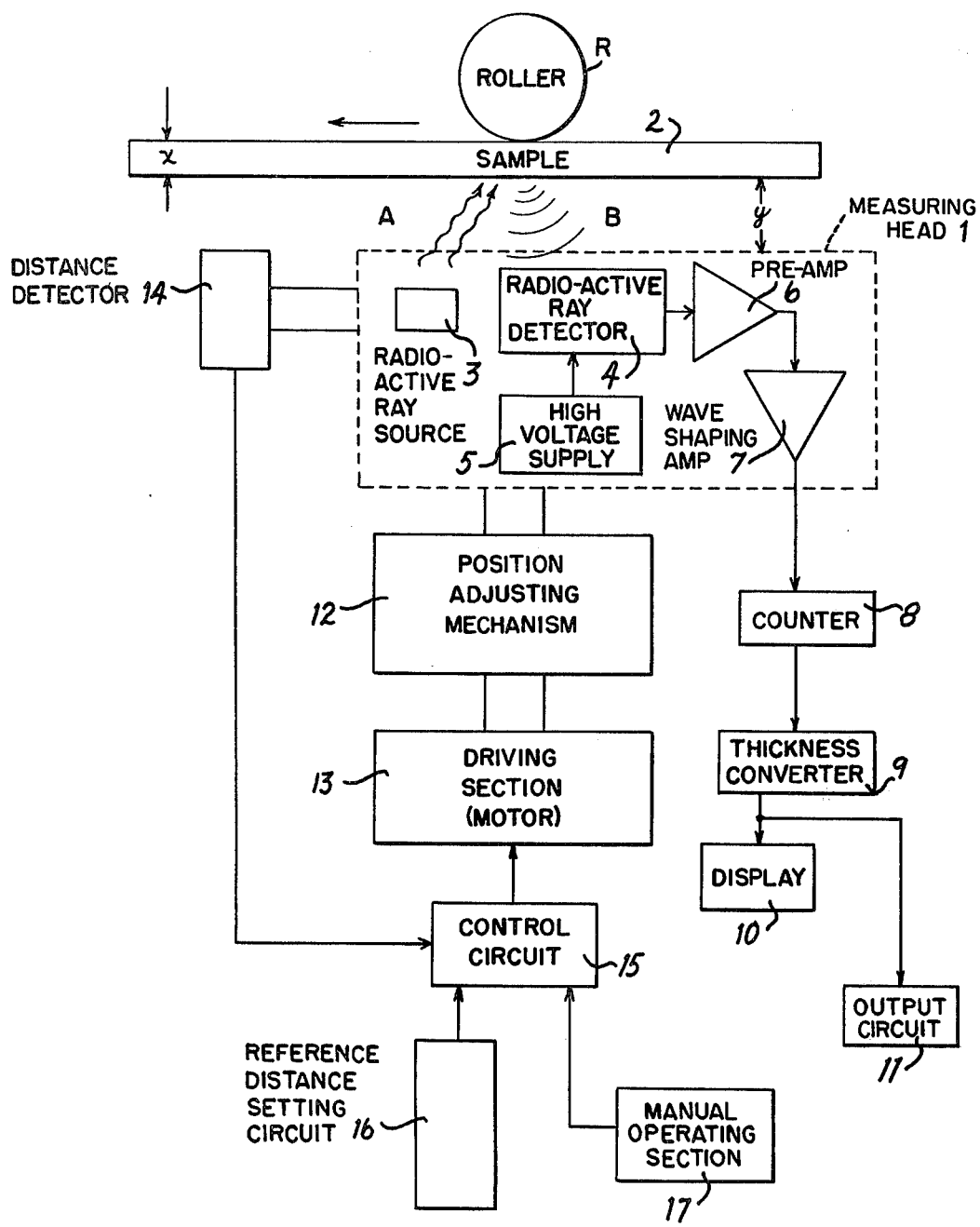
FIG. 1 is a schematic view showing the fundamental components of the radioactive ray gauge according to this invention.

Referring now to the drawings to describe one embodiment of this invention, FIG. 1 is a block diagram showing the fundamental structure of the radioactive ray gauge according to this invention.

The reference numeral 1 is a measuring head which includes a radioactive ray source 3 for radiating primary radioactive rays A to a sample sheet 2 having a coated layer thereon, a radioactive ray detector 4 such as a proportional counter or a scintillation counter is provided for detecting the secondary radioactive rays emitted from the sample, a high voltage supply 5 is connected to energize the radioactive ray detector 4, a pre-amplifier 6 amplifies the output signal of the radioactive detector 4 and a wave shaping amplifier 7 suitably shapes the amplified signal to eliminate noise components and delivers a signal of required level corresponding to the coated material on the sample and the signal is counted in a predetermined time by a counter 8.

This counted signal is converted to a representative of the thickness of the coated layer thickness signal by a thickness converter 9 and a display device 10 displays the thickness signal.

The thickness signal is also fed to an external output circuit 11 for connecting to the system controller.

The reference numeral 12 is a position adjusting mechanism provided for making the measuring head 1 reciprocate relative to the sample 2 in response to the output signal derived from a driving section 13 so that the distance between the surface of the sample 2 and the measuring head 1 is finely adjusted.

The position adjusting mechanism 12 comprises a cam or ball screw engaging with the motor of the driving section 13, and the cam or ball screw makes the casing of the measuring head fitted to the guide of the mechanism 12 slidably reciprocate relative to the sample 2.

The reference numeral 14 is a distance detector which is securely fixed to the measuring head 1.

This distance detector 14 is preferably a non-contact type displacement detector using the eddy-current phenomenon and detects continuously the distance between the measuring head 1 and the sample 2.

The distance signal derived from the distance detector 14 is fed to a control circuit 15. The control circuit 15 functions to control the driving section 13 to drive the position adjusting mechanism 12 so as to equalize the detected signal to the reference distance signal.

The control circuit 15 further receives the reference distance signal derived from a reference distance setting circuit 16 and also receives the output signal derived from a manual operating section 17.

In case that the reference distance setting circuit 16 acts, the signal detected by the distance detector 14 is compared with the reference distance signal in the control circuit 15. The control circuit 15 functions to control the driving section 13 to drive the position adjusting mechanism 12 so as to equalize the detected signal to the reference distance signal.

Accordingly, the position adjusting mechanism 12 makes the measuring head 1 move so that the relative position between the sample surface and the measuring head is maintained constant at the predetermined reference distance setting value.

If the position adjusting mechanism is operated at a high speed by the high power motor in the driving section 13, even abrupt distance variations between the sample surface and the measuring head can be suppressed by the adjustment in response to output signal of the distance detector.

Figure 2:
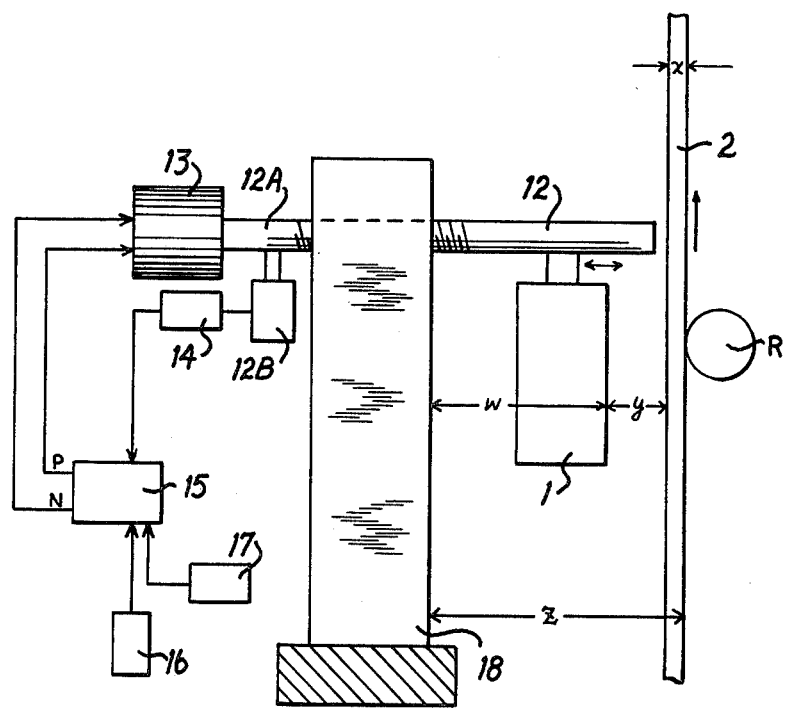

Referring next to FIG. 2, the measured sample 2 advances in the direction of the arrow with the rotation of the roller P. The fixed section 18 is positioned apart from the predetermined distance Z from the roller side surface of the sample 2.

The fixed section 18 has mounted thereon the position adjusting mechanism 12 including the ball screw which is driven by the driving section 13 including a pulse motor.

Accordingly, the ball screws 12 and 12A are rotated in equal amounts.

The pulse motor of the driving section 13 is controlled by the control circuit 15 including the position signal comparator which receives the output signal of the distance detector 14 for converting from the mechanical position signal of the detector to the electric signal.

The control circuit 15 generates either positive direction or negative direction pulses by comparing the output signal of the position detector 14 with that of the reference distance setting circuit 16 to accordingly control the direction of rotation of the driving section 13. Alternatively, the control circuit controls the driving section 13 independent of the position detector 14 in response to the output signal of the manual operating signal 17.

In case the sample sheet thickness variations, the change of distance between the sample and the measuring head, and the timing of the sheet thickness variations are anticipated, the manual operating section 17 makes the driving section 13 operate by the output signal thereof and makes the measuring head move closer to or farther apart from the sample 2 so that the distance between the sample surface and the measuring head is thereby compensated.

As mentioned above, the radioactive ray gauge according to this invention comprises the mechanism for adjusting and keeping the relative position between the measuring head and the sample surface corresponding to the reference distance constant, in response to the output of the distance detector which is provided on the measuring head.

Accordingly, in the gauge of the invention, there appear no variations in distance between the sample surface and the measuring head despite thickness variations of the sheet, the bending of the sample and the pass line flutter on the ON-Line system.

The radioactive ray gauge according to this invention is able to obtain precise measuring values and reduces the measuring time on ON-Line systems at a high speed since the intensity of the secondary radioactive ray is not lowered.

What is claimed is:

1. A radioactive ray gauge comprising: a measuring head disposed during use of the gauge in spaced-apart relationship from an advancing object which has at least a surface portion thereof coated with material and operable to emit primary radioactive rays directed toward the advancing object and to detect the intensity of secondary radioactive rays emitted by the coated material on the advancing object; a distance detector fixed to said measuring head for movement therewith and spaced apart from the advancing object for continuously detecting the distance between said measuring head and the surface of the advancing object and providing a corresponding output signal; a position adjusting mechanism operable when driven for selectively moving the combination of said measuring head and said distance detector toward and away from the advancing object; a driving motor connected to drive said position adjusting mechanism; and means including a control circuit for controlling the operation of said driving motor according to the output signal of said distance detector so as to maintain constant the distance between said measuring head and the surface of the advancing object.

2. A radioactive ray gauge according to claim 1; wherein said distance detector comprises an eddy-current type displacement detector.

* * * * *